United States Patent [19]

Bright

[11] Patent Number: 4,853,483

[45] Date of Patent: Aug. 1, 1989

[54] PREPARATION OF ALKYL THIOSEMICARBAZIDES

[75] Inventor: Danielle A. Bright, Spring Valley, N.Y.

[73] Assignee: ICI Americas Inc., Wilmington, Del.

[21] Appl. No.: 97,900

[22] Filed: Sep. 17, 1987

Related U.S. Application Data

[63] Continuation-in-part of Ser. No. 927,478, Nov. 6, 1986, Pat. No. 4,713,467.

[51] Int. Cl.$^4$ .................... C07C 159/00; C07C 155/08
[52] U.S. Cl. ........................................ 564/18; 558/235
[58] Field of Search .......................... 558/235; 564/18

[56] References Cited

U.S. PATENT DOCUMENTS

| | | | |
|---|---|---|---|
| 2,859,236 | 11/1958 | Schmidt et al. | 564/18 |
| 3,234,254 | 2/1966 | Soder et al. | 564/18 |
| 3,404,171 | 10/1968 | Ulrich | 564/18 |
| 3,637,788 | 1/1972 | Werth et al. | 564/18 |
| 3,787,472 | 1/1974 | Giesselmann et al. | 564/18 |
| 3,923,852 | 12/1975 | Zeiler et al. | 564/18 |
| 3,923,853 | 12/1975 | Zeiler et al. | 564/18 |
| 4,132,736 | 1/1979 | Cramm et al. | 564/18 |
| 4,237,066 | 12/1980 | Barton | 564/18 |
| 4,713,467 | 12/1987 | Telschow et al. | 558/18 |

FOREIGN PATENT DOCUMENTS

892790  3/1962  United Kingdom .................. 564/18

OTHER PUBLICATIONS

Delepine, Metallic Salts of Dithio Carbamic Acids: Preparation of Isothiocyanates . . . Chemical Abstracts, 1, 2236 (1907).
Jensen et al., Studies of Thioacids and Their Derivatives IX Thiosemicarbazides, Acta Chem. Scand., 22, 1–50 (1968).

*Primary Examiner*—John M. Ford
*Assistant Examiner*—Robert C. Whittenbaugh
*Attorney, Agent, or Firm*—Joel G. Ackerman

[57] ABSTRACT

The present invention relates to a process for the preparation of alkyl semicarbazides by reaction of a dithiocarbamate and hydrazine in a weakly basic reaction media using a metal rearrangement catalyst.

7 Claims, No Drawings

PREPARATION OF ALKYL THIOSEMICARBAZIDES

This is a continuation-in-part of U.S. Ser. No. 927,478, filed Nov. 6, 1986, now U.S. Pat. No. 4,713,467 entitled "Process for Production of Isothiocyanates".

BACKGROUND OF THE INVENTION

1. Field of the Invention

This invention relates to the preparation of alkyl thiosemicarbazides by reaction of hydrazine with a dithiocarbamate.

2. Description of the Prior Art

Alkyl thiosemicarbozides are intermediates of the formula RNHC (S) NHNH$_2$ with R preferably being lower alkyl of from 1 to 4 carbon atoms.

U.S. Pat. No. 4,132,736 to G. Cramm et al. indicates that alkyl thiosemicarbazides can be formed if a hydrazinium salt of the corresponding N-alkyl dithiocarbamic acid is heated in a solvent in the presence of sulfur, optionally in the presence of hydrazine hydrate, under conditions which pull off hydrogen sulfide and ammonia from the reaction environment.

More recently, U.S. Pat. No. 4,237,066 to D. B. Barton described a procedure for forming alkyl thiosemicarbazides by steam distilling water off from an aqueous solution containing hydrazine and an N-lower alkyldithiocarbamic acid quaternary ammonium salt thereby effecting pyrolysis while distilling off water, alkyl amine and hydrogen sulfide, and cooling the distillant to form crystals of the desired alkyl thiosemicarbazide.

SUMMARY OF THE PRESENT INVENTION

The present invention involves a process for preparing alkyl thiosemicarbazides by reacting a dithiocarbamate and hydrazine under weakly basic conditions in the presence of a metal rearrangement catalyst.

DETAILED DESCRIPTION OF THE PRESENT INVENTION

The dithiocarbamate starting material intended for use in the instant process has the formula RNHC (S) SA, with R preferably being lower alkyl of from 1 to 4 carbon atoms and A being a cation such as ammonium or alkali metal (sodium, potassium, etc.) or even alkaline earth metal if desired. An exemplary compound is sodium N-methyl dithiocarbamate which is commercially available under the trademark VAPAM from Stauffer Chemical Company.

Hydrazine has the formula NH$_2$NH$_2$ and can be reacted in the form of its hydrate (NH$_2$NH$_2$.H$_2$O) if desired. The term "hydrazine" is intended to cover all forms of hydrazine which are reactive with a dithiocarbamate to form an alkyl thiosemicarbazide in accordance with the present invention. Hydrazine compounds which are useful in connection with the present invention include hydrazine acetate, hydrazine dihydrochloride, hydrazine monohydrochloride, hydrazine sulfate, and dihydrazine sulfate.

The relative weight amounts of these two reactants (on a 100% active basis) can range from about 1:1 to about 1:1.2 on a molar basis. The reaction is preferably carried out at temperatures of from about 70° C. to about 105° C. in an aqueous reaction medium at pH values which are neutral or weakly basic (e.g., from about 7 to about 9).

Yields of the desired alkyl thiosemicarbazides, in the above type of reaction, are enhanced if: (1) a metal rearrangement catalyst is employed; and (2) if the pH of the reaction medium is kept weakly alkaline.

The metal rearrangement catalyst employed in the present process embraces those used as metal oxidation catalysts in U.S. Ser. No. 927,478, filed Nov. 6, 1986, which is incorporated herein by reference. Included are such metals as manganese, iron, copper, zinc, cobalt, and molybdenum or one or more of the water soluble salts of such metals. Representative amounts for such a catalyst range from about 0.005% to about 0.5% by weight of the amount of reactant.

The metal rearrangement catalyst used in the instant process catalyzes the rearrangement of the hydrazinium salt in the second step of the reaction, whereas controlling the pH in the weakly alkaline range (e.g., by the addition of an acid such as sulfuric acid) speeds up the formation of the hydrazinium salt in the first step. The following equations show how the step-wise reaction proceeds:

First Step

Second Step

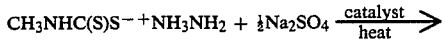

CH$_3$NHC(S)NHNH$_2$ + H$_2$S

The pH of the reaction medium should also be maintained weakly basic, e.g., preferably from about 8–9. This usually will require the addition of an appropriate amount of an acid (e.g., a strong mineral acid such as sulfuric acid) to adjust the pH downwardly from the strongly basic (e.g., pH=12) region resulting from admixture of hydrazine and dithiocarbamate.

The present invention is further described in the Examples which follow.

EXAMPLE 1

This Example illustrates one embodiment of the present invention.

To an aqueous solution containing 2 moles of sodium methyl-dithiocarbamate (788.8 grams of 32.7% VAPAM soil fumigant) was added 1.2 mole of hydrazine monohydrate (60 grams). At the end of the addition, the temperature of the reaction mixture was 30° C. and the pH was about ~12. The pH was then lowered to 8.5 by addition of concentrated H$_2$SO$_4$ and 1.16 grams of MnSO$_4$.H$_2$O, dissolved in 5 ml of water, was then added. The reaction mixture was heated to reflux (95°–105° C.) while passing nitrogen through the reaction environment, until no more H$_2$S was evolved (after 11–13 hours). Additional H$_2$SO$_4$ was added throughout the reaction to maintain a pH of 8.5. The reaction mixture was then filtered hot, and the filtrate was allowed to crystallize. The crystals were filtered and were washed with 150 ml of cold water. After drying, there was obtained 172.9 grams of solid (82.3% yield) 4-methyl-3-thiosemicarbazide melting at 131°–133° C.

COMPARATIVE EXAMPLE 2

This Example illustrates the results obtained without use of a manganese sulfate rearrangement catalyst.

To an aqueous solution containing 0.48 mole of sodium methyl dithiocarbamate (191.5 grams of 32.7% VAPAM soil fumigant) was added 0.6 mole of $NH_2NH_2.H_2O$ (30 grams). The pH was adjusted to 8.5 by addition of concentrated $H_2SO_4$. The reaction mixture was then heated to reflux (95°–105° C.) while passing $N_2$ through the reaction environment for 13 hours. Additional $H_2SO_4$ was added throughout the reaction to maintain a pH of 8.5. The reaction mixture was filtered hot, and the filtrate was then allowed to crystallize. Upon filtration and drying, there was obtained 34.7 grams (68.8% yield) of solid 4-methyl-3-thiosemicarbazide melting at 131°–133° C.

p COMPARATIVE EXAMPLE 3

This Example illustrates the results obtained when the pH is not controlled in the weakly alkaline region.

To an aqueous solution containing 0.48 mole of sodium methyl dithiocarbamate (191.5 grams of 32.7% VAPAM soil fumigant) was added 0.6 mole of hydrazine monohydrate (30 grams) and 290 mg of $MnSO_4.H_2O$. The reaction mixture was refluxed (105° C.) for 11 hours while passing $N_2$ through the reaction medium. The reaction mixture was filtered hot, and the filtrate was allowed to crystallize. Upon filtration and drying, there was obtained 3.6 grams (63% yield) of 4-methyl-3-thiosemicarbazide.

The foregoing represent certain embodiments of the present invention but should not be construed in a limiting sense. The scope of protection sought is set forth in the claims which follow.

I claim:

1. A process for preparing alkyl thiosemicarbazides which comprises reacting an alkyl dithiocarbamate and hydrazine at a pH of from about 7 to about 9 in the presence of a catalytically effective amount of a metal rearrangement catalyst.

2. A process as claimed in claim 1 wherein the alkyl is a lower alkyl of from 1 to 4 carbon atoms.

3. A process as claimed in claim 1 wherein the hydrazine is hydrazine hydrate.

4. A process as claimed in claim 1 wherein the pH is from about 8 to about 9 and is achieved by the addition of acid.

5. A process as claimed in claim 1 wherein the alkyl is lower alkyl and the pH is achieved by the addition of acid.

6. A process as claimed in claim 1 wherein the metal rearrangement catalyst is a metal of water soluble salt thereof and catalyzes the rearrangement of the hydrazinium salt of the dithiocarbamate to the alkyl semicarbazide.

7. A process as claimed in claim 5 wherein the metal rearrangement catalyst is a metal or water soluble salt thereof and catalyzes the rearrangement of the hydrozinium salt of the dithiocarbamate to the alkyl semicarbazide.

* * * * *